(12) United States Patent
Plachta et al.

(10) Patent No.: US 10,569,085 B2
(45) Date of Patent: Feb. 25, 2020

(54) IMPLANTABLE ELECTRODE CONFIGURATION

(71) Applicant: Neuroloop GmbH, Freiburg (DE)

(72) Inventors: Dennis Plachta, Voerstetten (DE); Mortimer Giehrtmuehlen, Freiburg (DE); Thomas Stieglitz, Freiburg (DE); Josef Zentner, Freiburg (DE)

(73) Assignee: Neuroloop GmbH, Freiburg (DE)

( * ) Notice: Subject to any disclaimer, the term of this patent is extended or adjusted under 35 U.S.C. 154(b) by 301 days.

(21) Appl. No.: 15/517,890

(22) PCT Filed: Oct. 7, 2015

(86) PCT No.: PCT/EP2015/073132
§ 371 (c)(1),
(2) Date: Apr. 7, 2017

(87) PCT Pub. No.: WO2016/055514
PCT Pub. Date: Apr. 14, 2016

(65) Prior Publication Data
US 2017/0326362 A1 Nov. 16, 2017

(30) Foreign Application Priority Data
Oct. 7, 2014 (DE) .......................... 10 2014 014 943

(51) Int. Cl.
*A61N 1/05* (2006.01)
*A61N 1/36* (2006.01)
(Continued)

(52) U.S. Cl.
CPC ............. *A61N 1/3605* (2013.01); *A61N 1/05* (2013.01); *A61N 1/059* (2013.01); *A61N 1/326* (2013.01); *A61N 1/057* (2013.01); *A61N 1/37247* (2013.01)

(58) Field of Classification Search
CPC ....................................................... A61N 1/05
(Continued)

(56) References Cited

U.S. PATENT DOCUMENTS 5,215,088 A 6/1993 Normann et al.
5,919,220 A 7/1999 Stieglitz et al.
(Continued)

FOREIGN PATENT DOCUMENTS

DE 44 33 111 A1 3/1996
DE 10 2011 078 982 A1 1/2013

OTHER PUBLICATIONS

International Search Report for PCT/EP2015/073132 dated Jan. 14, 2016; English translation submitted herewith (5 pages).
(Continued)

*Primary Examiner* — Stanley Tso
(74) *Attorney, Agent, or Firm* — Fitch, Even, Tabin & Flannery LLP

(57) ABSTRACT

The invention is an implantable electrode configuration having a carrier substrate of a biocompatible polymer in at least some areas and a freely accessible electrode surface applied to the carrier substrate or integrated into the carrier substrate on the carrier substrate surface in at least some areas is described and a method for producing the implantable electrode configuration. The electrode has a metallic base plate having a planar top side and bottom side, including at least one structural element protruding orthogonally from the top side. The planar surface of the metallic base plate is oriented parallel to the carrier substrate surface and the metallic base plate is enclosed by the biocompatible polymer, except for a first surface area of the at least one structural element which faces the carrier substrate surface and is the freely accessible electrode surface.

25 Claims, 2 Drawing Sheets

(51) Int. Cl.
    *A61N 1/32*     (2006.01)
    *A61N 1/372*    (2006.01)
(58) Field of Classification Search
    USPC .......................................................... 174/250
    See application file for complete search history.

(56) References Cited

U.S. PATENT DOCUMENTS

| | | |
|---|---|---|
| 2009/0124965 A1 | 5/2009 | Greenberg et al. |
| 2010/0307803 A1* | 12/2010 | Paul .......................... B32B 7/12 174/257 |
| 2011/0038130 A1 | 2/2011 | Hogg et al. |
| 2012/0296444 A1 | 11/2012 | Greenberg et al. |
| 2014/0128954 A1 | 5/2014 | Schüttler et al. |
| 2014/0194950 A1 | 7/2014 | Greenberg et al. |

OTHER PUBLICATIONS

Written Opinion of the International Searching Authority or PCT/EP2015/073132 dated Jan. 14, 2016; English translation submitted herewith (11 pages).

* cited by examiner

IMPLANTABLE ELECTRODE CONFIGURATION

CROSS-REFERENCE TO RELATED APPLICATIONS

Reference is made to International Application No. PCT/EP2015/073132 filed Oct. 7, 2015, and German Patent Application No. 102014014943.9, filed Oct. 7, 2014, which applications are incorporated herein by reference in their entirety.

BACKGROUND OF THE INVENTION

Field of the Invention

The invention relates to an implantable electrode configuration with a carrier substrate of biocompatible polymer or polyimide in at least some areas, and a freely accessible electrode surface of an electrode applied to the carrier substrate or integrated into the carrier substrate present on the carrier substrate surface in at least some areas.

Description of the Prior Art

Medical implants used for the purpose of at least one of supplying and diverting at least one of electrical signals into and/or out of regions located intracorporeally usually have metallic line structures with freely accessible electrode surfaces, which come into direct contact with the intracorporeal tissue areas to be at least one of stimulated electrically and monitored. The wet intracorporeal medium to which the medical implants are exposed makes high demands on the stability of the material as well as the lifetime of the electrode structures applied to or onto a carrier substrate of an implant. Thus, intracorporeal liquids, for example, have a tendency to penetrate into extremely small cracks and interspaces on technical-grade surfaces in particular due to their capillary spreading and wetting properties, so that electrode structures, which are applied mainly to carrier substrate surfaces and enclose an interface that is constantly exposed to the capillary fluid, are constantly exposed to a fluid-mechanical releasing effect because of the difference in material between the carrier substrate of at least one biocompatible polymer and the metallic electrode material. Even a microcrack developing in the interface between the electrode structure and the carrier structure can result in separation of the electrode structure from the polymer carrier structure, so that the medical implant can penetrate into polymer carrier materials of an implant over a period of time even when the surfaces are free of cracks.

German Patent DE 10 2011 078 982 A1 describes an implantable neural electrode configuration, in which the connecting electrode surfaces as well as neural contact electrode surfaces are each surrounded by an electrically insulating biocompatible substrate, into which the two electrode surfaces of electrically interconnected conductor paths are completely integrated. The planar and freely accessible electrode surfaces are surrounded like a frame by a sheathing made of a mechanically strong polymer, which provides good electrical insulation.

The publication DE 44 33 111 A1 describes a cuff electrode having a plurality of electrode pins elevated above a flexible multilayer substrate made of nonconductive silicone. The pins are electrically contacted by printed conductors running inside the substrate. The electrode pins are designed for the purpose of penetrating into a nerve fiber bundle, around which the cuff electrode can be placed in the form of a peripheral wrapping.

With all known embodiments of implantable electrode structures, no measures have been taken to effectively counteract the above-mentioned problem of liquid-induced degradation (delamination) of the composite between the electrode body and the carrier structure matrix surrounding the electrode body. In addition, no measures are described for increasing the mechanical fastening of the metal-polymer hybrid in the area of a non-planar structure.

SUMMARY OF THE INVENTION

The invention is an improvement of an implantable electrode configuration having a carrier substrate made of a biocompatible polymer or polyimide in at least some areas, a freely accessible electrode surface of an electrode applied to the carrier substrate or integrated into the carrier substrate present on the carrier substrate surface in at least some areas, so that the intracorporeal separation process that takes place in a creeping manner between the electrode and the carrier substrate is at least significantly reduced or is prevented entirely.

The implantable electrode configuration according to the invention with a carrier substrate of a biocompatible polymer in at least some areas, with a freely accessible electrode surface of an electrode applied to the carrier substrate or integrated into the carrier substrate being present in at least some areas, is characterized by the electrode having a metallic base plate with a planar top side and bottom side, at least one structural element that protrudes locally beyond the top side of the base plate which is orthogonal to the base plate. The planar surface of the metallic base plate is arranged so that it has a parallel orientation to the carrier substrate surface. Furthermore, the metallic base plate and the at least one structural element, which is connected to the base plate, preferably monolithically, is completely surrounded by the biocompatible polymer directly and indirectly, except for a first surface area of the at least one structural element, which is oriented to face the carrier substrate surface and which corresponds to the freely accessible electrode surface.

The implementation according to the invention of a connection between the electrode and at least one of the biocompatible polyimide and polymer material of the carrier substrate with the greatest possible long-term stability is reflected in a special structural design of the electrode and in a special integration of the electrode into the carrier substrate, which is thereby made possible, so that at least one of the wet intracorporeal medium and the intracorporeal liquid has only a minor opportunity to penetrate into the interfaces between the metallic electrode material and the biocompatible polymer of the carrier substrate and to apply a load to it. The interfacial lengths exposed to the moisture are minimized in this way. This is achieved by the fact that most of the electrode body is surrounded by the biocompatible polymer, with only at least one of a small electrode surface area and a plurality of electrode areas of small dimensions are arranged in a freely accessible manner on the carrier substrate surface for the purpose of electrical signal transmission and are exposed to the intracorporeal medium, forming minimal interfacial lengths. If some of the liquid should happen to degrade the interface over a period of time, so that the liquid is capable of penetrating into the interfacial depths in at least some areas, then the structured electrode body according to the invention has additional features, which help to prevent a loss of function of the medical implant.

According to the invention, the electrode provides a metallic base plate, preferably made of platinum, with a planar top side and bottom side, with at least one structural element, preferably multiple structural elements, which protrude above the top side of the base plate orthogonally and locally and are preferably designed in the form of columns, ribs, sleeves or webs. The at least one structural element is connected monolithically to the base plate and is preferably manufactured from a material that has a very high electrical charge transfer capacity, which is preferably iridium oxide. The metallic base plate is completely enclosed by the biocompatible polymer of the carrier substrate, as is the at least one structural element, but with the exception of the first surface area of the structural element which is oriented to face the carrier substrate surface and preferably does not protrude beyond it.

Therefore, this reduces the electrode contact area that is freely accessible on the carrier substrate surface but is completely surrounded by biocompatible polymer of the carrier substrate because of the hermetic enclosure of the base plate as well as the structural elements connected thereto in one piece except for the surface areas oriented to the face the carrier substrate surface. Penetration of at least one of liquid and moisture due to the medium between the electrode body and the biocompatible polymer of the carrier substrate is thus made much more difficult. In another preferred embodiment, an adhesion promotion layer or an adhesion promotion layer configuration, for example, in the form of SiC or DLC, is preferably also introduced between the bottom side of the metallic base plate and the biocompatible polymer of the carrier substrate, which enters into covalent bonding with the polymer carrier substrate as well as with the metallic material of the electrode. In this way, the layers are chemically bonded to one another, so that possible microcavities, which can usually develop in the case of direct application of a metal layer to a polymer surface, for example, by sputtering or vapor deposition, are prevented. Precisely such microcavities can fill up with water over a period of time due to the penetration effect of molecular water into polymer materials, thereby possibly leading to a local detachment of at least one of the metal layer and the electrode.

It can be concluded from the further description with reference to specific preferred embodiments that it has proven to be advantageous to at least one of cover and provide an adhesion promotion layer at least on all the surface areas of the electrode at least facing away from the carrier substrate surface.

In another specific embodiment, the at least one structural element has at least one protrusion in the form of a web, oriented orthogonal to the longitudinal extension of the structural element and arranged at a distance from the carrier substrate surface so that the protrusion is surrounded by the biocompatible polymer. The protrusion also has surface areas oriented in parallel with the top side of the base plate. The surface areas facing the top side of the base plate preferably are provided with an adhesion promotion layer or an adhesion promoter layer configuration. All of the surface areas of the electrode body that are oriented preferably parallel to at least one of the top side and bottom side of the base plate, horizontally, may of course also be coated with an adhesion promotion layer or an adhesion promotion layer configuration.

Additional preferred specific embodiments, with respect to a possible design of the electrode structure, are now explained in conjunction with the following figures.

BRIEF DESCRIPTION OF THE DRAWINGS

The invention is described below on the basis of exemplary embodiments without restricting the general idea of the invention, with reference to the drawings, in which.

DETAILED DESCRIPTION OF THE INVENTION

Figure 1:
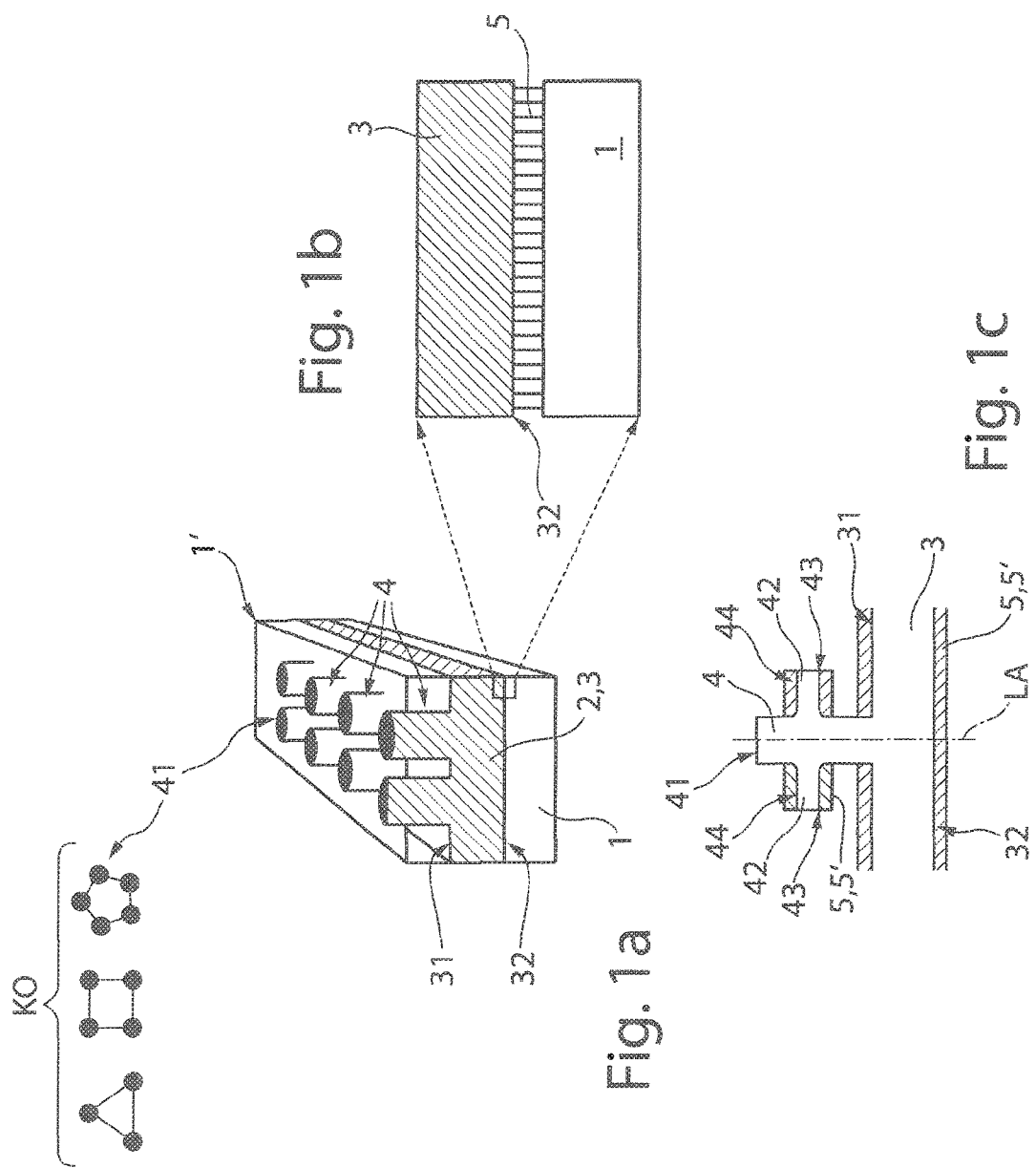
FIG. 1a shows a detailed diagram of an electrode integrated into the carrier substrate.
FIG. 1b shows an alternative design of a structural element.

To permanently improve the joining of an electrode body 2, for example, in the form of an electrode strip in or on a carrier substrate 1 made of a biocompatible polymer material, the electrode strip 3 is integrated extensively into the carrier substrate 1 in the following manner as shown in FIG. 1a.

The electrode body 2 has a metallic base plate 3, which has a top side 31 and a bottom side 32. Orthogonally elevated structural elements 4 are connected in one piece to the top side 31 of the base plate 3 and are preferably distributed over the entire area of the top side. These structural elements preferably are in the form of protrusions shaped like columns, ribs, webs or sleeves, over a surface area 41 facing the carrier substrate surface 1' as shown in FIG. 1a, which can come into direct contact with the epineurium, for example, of a nerve fiber bundle in the implanted state of the electrode configuration. In addition, an adhesion promotion layer 5 is advantageously provided at least between the bottom side 32 and the polymer material of the carrier substrate 1 surrounding the base plate 3 as seen in FIG. 1b, which shows enlarged detail of the implantable electrode configuration diagrammed in FIG. 1a.

Furthermore, the adhesion promotion layer 35 may also be applied to the top side 31 of the base plate 3. Especially suitable adhesion promoter layers are silicon carbide (SiC) and diamond-like carbon (DLC). The electrode bodies 2, in particular in the area of the structural elements 3, preferably contain iridium oxide, which is one of the materials having the highest charge transfer capacities.

Basically, any number and configuration of individual structural elements 4 may be selected, but constellations KO arranged geometrically, such as square, pentagonal, hexagonal or higher-order configuration patterns, are also suitable, as for example, those shown in FIG. 1a.

A further improved variant of the at least one structural element 4 is illustrated in FIG. 1c. FIG. 1c shows a longitudinal section through a structural element 4, which has a longitudinal extension LA oriented orthogonally to the top side 31 of the metallic base plate 3. The structural element 4 has, along the longitudinal extension, at least one lateral protrusion 42 having an extension oriented orthogonally to the longitudinal axis LA.

The protrusion 42 has a second surface area 43, which is oriented parallel to the top side 31 of the metallic base plate 3 and faces it. In a first variant, the adhesion promotion layer 5 or an adhesion promotion layer configuration 5' is applied to the second surface area 43 and is also provided on the bottom side 32 as in the present case. The second surface area 43 is disposed spaced from the first surface area 31 and is completely surrounded by the biocompatible polymer while separated by at least one of the adhesion promotion layer (5) and the adhesion promotion layer configuration (5').

In a second variant, at least one of the adhesion promotion layer (5) and the adhesion promotion layer configuration (5') is additionally applied to the top side 44 of the protrusion 42, which is shaped as a web and is preferably also applied to the top side 31 of the base plate 3.

To produce the at least one electrode 2 according to the invention, which is inserted into the biocompatible polymer material, the process steps are explained with reference to the sequential images a through ab.

A polyimide layer PI is applied in a uniform distribution to the surface of a silicon wafer Wa that is supplied at step a by spin coating at step b. Then a photoresist Fl at step c is applied to the polyimide layer Pl which is next exposed with the help of a mask and developed for the purpose of structuring the photoresist Fl as seen at step d. In the next step, an adhesion promoter layer HV is applied over the entire area, as for example, by a vapor deposition technique deposited there. DLC, for example, is suitable for this purpose. Metallization over the entire surface area is performed with step f, preferably with platinum Pt, which is deposited on the adhesion promotion layer HV by sputtering or vapor deposition processes. The base plate 3 of the electrode identified above is created in this way. A lift-off process is carried out at the next step g, in which all the material layers are removed except for the structured platinum base plate Pt, which is applied to the polyimide layer Pl with the adhesion promotion layer HV on the bottom side.

An adhesion promotion layer HV is applied again in step h. Then a second polyimide layer PI is deposited by spin coating at step i. In step j, a photoresist layer Fl is applied again by spin coating. Next, the photoresist layer Fl is exposed and developed by using a mask at step k. Then in the next step l, the photoresist layer Fl is removed locally down to the top adhesion promotion layer by dry plasma etching in the area of the opened photoresist layer.

In step m, an Ir-IrOx layer is applied again. In step n, the structured photoresist layer Fl is extracted by a lift-off process. In the next step o, a photoresist layer Fl is applied. In step p, this photoresist layer Fl is developed and etched down to the level of the Ir-IrOx layer. It should be pointed out that the opening exceeds the width of the Ir-IrOx area of the electrode as seen at step p. An adhesion promotion layer HV is applied again at step q. At step r, a third metallization is performed by at least one of sputtering and vapor deposition. In this step, iridium Ir is deposited with an increasing amount of iridium oxide IrOx in the direction vertically upward. In the next step s, an HV layer is applied again. In step t, a lift-off process is again performed at in which the metal layer applied to the polyimide surface is locally removed.

Large-area deposition of a polyimide layer Pl then takes place by spin coating at process step u. In the following step v, this layer is covered with a photoresist layer Fl, which is then exposed and developed using a mask in step w, so that a local opening is formed within the photoresist layer. In the next step x, Ir-IrOx is again applied by sputtering to form the protrusion 42 identified above. A lift-off process takes place in process step y, followed by step z, in which a photoresist layer Fl is applied by spin-coating.

Figure 2:
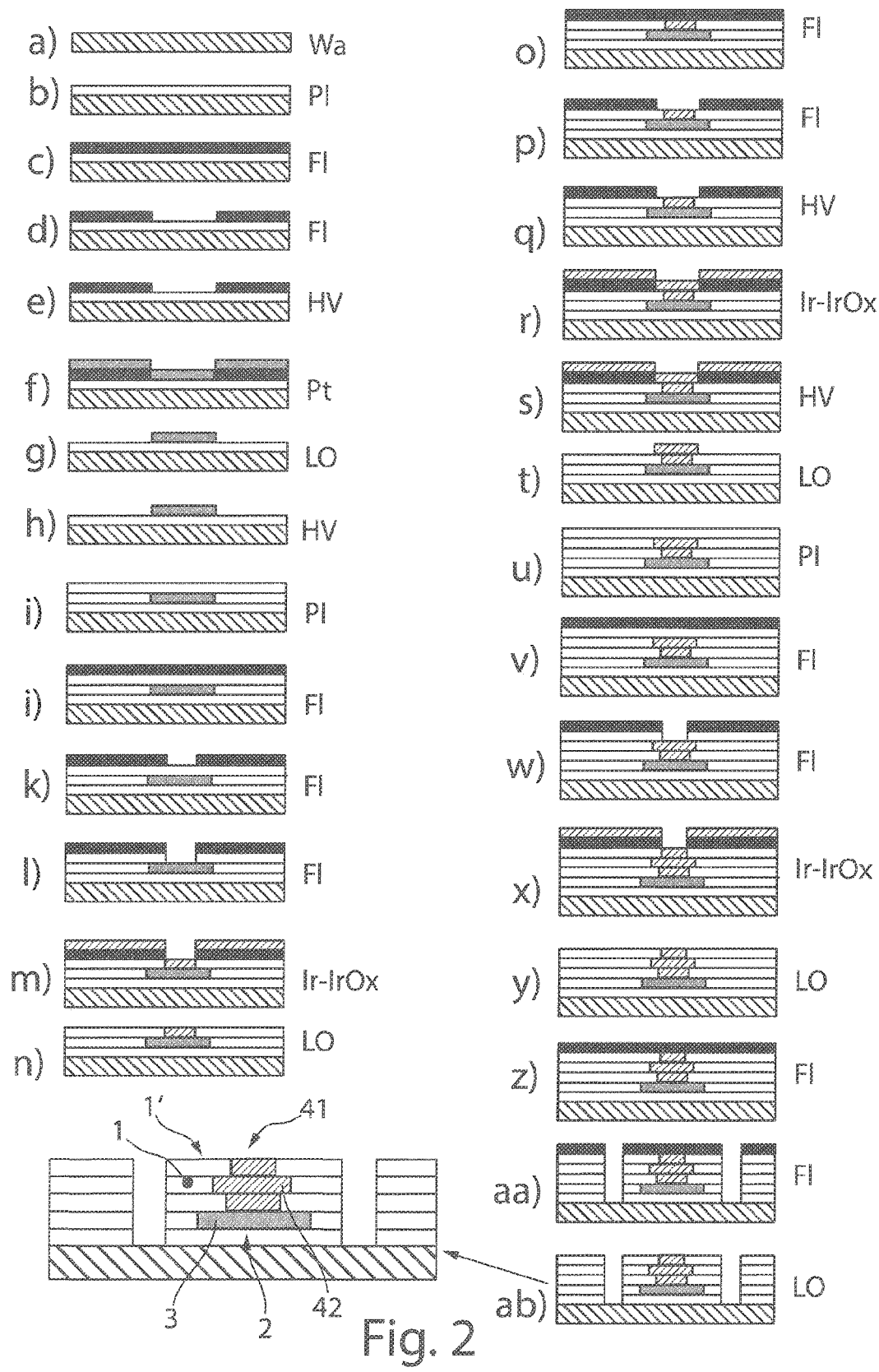
FIG. 2 shows sequential diagrams for the production of the implantable electrode configuration.

In step aa), these photoresist Fl is developed by using a mask. Two trenches extending to the surface of the silicon wafer Wa are exposed by dry etching. In the last step ab), the photoresist layer Fl is removed, which creates an implantable electrode configuration providing an electrode body 2, which is covered almost completely by polyimide. The electrode body has a base plate 3 made of platinum and a web-type protrusion 4 having a top electrode surface 41 which is freely accessible as shown by the enlarged diagram in FIG. 2.

With the method described above, it is possible to produce the base plate having a plate thickness between 10 nm and 5 μm, on which structural elements having an elevated length of 50 nm to 5 μm.

In a preferred configuration of the base plate 3 inside the carrier substrate, which is made of the individual polyimide layers Pl, the base plate 3 is situated centrally within the carrier substrate. The goal is to form the first polyimide layer at step a) so that the thickness is enough to correspond to the total thickness of the additional polyimide layers Pl, which are applied at steps i) and u). This configuration of the base plate 3 has the experimentally verifiable advantage which is that compensation is provided for inherent stresses which develop during a subsequent tempering process acting on the base plate. The tempering process is required to provide a material prestress into the carrier substrate, as a result of which the implantable cuff is capable of winding itself automatically around the nerve fiber bundle.

REFERENCE LIST 1 carrier substrate
1' carrier substrate surface
2 electrode
3 base plate
31 top side
32 bottom side
4 structural element
41 first surface area
42 web-type protrusion
43 second surface area
44 third surface area
5 adhesion promotion layer
5' adhesion promotion layer configuration
KO constellation
LA longitudinal extent

The invention claimed is:

1. An implantable electrode configuration having a carrier substrate comprising a one piece biocompatible polymer located in at least part of the substrate in which an accessible electrode surface of an electrode is applied to the carrier substrate or is integrated into the carrier substrate in at least part of the carrier substrate surface, comprising:

a metallic base plate having a planar surface with a top side and bottom side, at least one structural element protruding relative to the top side and the planar surface of the metallic base plate being oriented parallel to the carrier substrate surface;

and wherein the metallic base plate in combination with the at least one structural element are completely enclosed by the one piece biocompatible polymer, except for a first surface area of the at least one structural element which is oriented to face away from the carrier substrate surface and corresponds to the accessible electrode surface to provide a complete enclosure of the base plate and the electrode except for any surfaces facing the carrier surface;

wherein the at least one structural element includes a longitudinal extension oriented orthogonal to the top side of the metallic base plate, along the longitudinal extension the at least one structural element has at least one web which protrudes orthogonal relative to the longitudinal extension and includes a second surface area parallel to the top side of the metallic base plate and to which an adhesion promotion layer is applied thereto;

and the second surface area is separated from the first surface area and is surrounded by the biocompatible polymer;

and wherein the carrier substrate has a thickness oriented orthogonal to the carrier substrate surface and the base plate is centrally located relative to the substrate thickness.

2. The electrode configuration according to claim 1, comprising:
an adhesion promotion layer located at least between the bottom side of the metallic base plate and the biocompatible polymer of the carrier substrate.

3. The electrode configuration according to claim 2, comprising:
the at least one structural element is connected in one piece to the metallic base plate.

4. The electrode configuration according to claim 3, comprising:
identical structural elements located on the top side of the metallic base plate in a geometric pattern.

5. The electrode configuration according to claim 4, wherein:
the at least one structural element is one of columns, ribs, sleeves or webs.

6. The electrode configuration according to claim 3, wherein:
the at least one structural element is one of columns, ribs, sleeves or webs.

7. The electrode configuration according to claim 2, comprising:
identical structural elements located on the top side of the metallic base plate in a geometric pattern.

8. The electrode configuration according to claim 7, wherein:
the at least one structural element is one of columns, ribs, sleeves or webs.

9. The electrode configuration according to claim 2, wherein:
the at least one structural element is one of columns, ribs, sleeves or webs.

10. The electrode configuration according to claim 2, wherein:
the base plate has a thickness ranging between 10 nm and 5 µm, and the at least one structural element has a length at a location above the base plate ranging between 50 nm and 5 µm.

11. The electrode configuration according to claim 1, comprising:
the at least one structural element is connected in one piece to the metallic base plate.

12. The electrode configuration according to claim 11, comprising:
identical structural elements located on the top side of the metallic base plate in a geometric pattern.

13. The electrode configuration according to claim 12, wherein:
the at least one structural element is one of columns, ribs, sleeves or webs.

14. The electrode configuration according to claim 11, wherein:
the at least one structural element is one of columns, ribs, sleeves or webs.

15. The electrode configuration according to claim 11, wherein:
the base plate has a thickness ranging between 10 nm and 5 µm, and the at least one structural element has a length at a location above the base plate ranging between 50 nm and 5 µm.

16. The electrode configuration according to claim 1, comprising:
identical structural elements located on the top side of the metallic base plate in a geometric pattern.

17. The electrode configuration according to claim 16, wherein:
the at least one structural element is one of columns, ribs, sleeves or webs.

18. The electrode configuration according to claim 16, wherein:
the base plate has a thickness ranging between 10 nm and 5 µm, and the at least one structural element has a length at a location above the base plate ranging between 50 nm and 5 µm.

19. The electrode configuration according to claim 1, wherein:
the at least one structural element is one of columns, ribs, sleeves or webs.

20. The electrode configuration according to claim 19, wherein:
the base plate has a thickness ranging between 10 nm and 5 µm, and the at least one structural element has a length at a location above the base plate ranging between 50 nm and 5 µm.

21. The electrode configuration according to claim 1, wherein: the second surface area faces away from the carrier substrate surface.

22. The electrode configuration according to claim 21, wherein:
the base plate has a thickness ranging between 10 nm and 5 µm, and the at least one structural element has a length at a location above the base plate ranging between 50 nm and 5 µm.

23. The electrode configuration according to claim 1, wherein:
the base plate has a thickness ranging between 10 nm and 5 µm, and the at least one structural element has a length at a location above the base plate ranging between 50 nm and 5 µm.

24. A method for producing a implantable electrode configuration according to claim 1, comprising:
applying a metallic base plate to a carrier substrate of the biocompatible polymer;
applying monolithically at least one structural element which extends orthogonally from the top side of the base plate; and
applying the biocompatible polymer to the carrier substrate and the base plate so that the at least one structural element, except for a first surface area of the at least one structural element, is oriented to face away from the top side of the base plate and is completely surrounded by the biocompatible polymer.

25. The method according to claim 24, comprising:
depositing the at least one structural element by a vapor deposition or sputtering.

* * * * *